US00PP25890P3

(12) United States Plant Patent
Leis et al.

(10) Patent No.: US PP25,890 P3
(45) Date of Patent: Sep. 15, 2015

(54) APPLE TREE NAMED 'MAJESTY'

(50) Latin Name: ***Malus domestica* Mill.**
Varietal Denomination: Majesty

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara (IT); Alessio Martinelli, Ferrara (IT); Francesco Tagliani, Argenta (IT); Gianfranco Castagnoli, Quingentole (IT)

(73) Assignee: C.I.V.—CONSORZIO ITALIANO VIVAISTI—SOCIETA CONSORTILE A R.L., Comacchio FE (IT)

( * ) Notice: Subject to any disclaimer, the term of this patent is extended or adjusted under 35 U.S.C. 154(b) by 193 days.

(21) Appl. No.: 13/986,175

(22) Filed: Apr. 9, 2013

(65) Prior Publication Data

US 2013/0269068 P1 Oct. 10, 2013

(30) Foreign Application Priority Data

Apr. 10, 2012 (QZ) ..... PBR 2012/0807

(51) Int. Cl.
*A01H 5/08* (2006.01)

(52) U.S. Cl.
USPC ..... Plt./161
CPC ..... *A01H 5/0875* (2013.01)

(58) Field of Classification Search
USPC ..... Plt./161, 172
CPC ..... A01H 5/0875; A01H 5/08
See application file for complete search history.

*Primary Examiner* — Kent L Bell
(74) *Attorney, Agent, or Firm* — Foley & Lardner LLP

(57) ABSTRACT

A new and distinct *Malus domestica* Mill. apple tree variety named 'Majesty' particularly characterized by a medium-low vigorous tree with high and consistent production. The fruit is of medium-big size, with globose regular shape. The color is attractive red, covered on 80-90% of the surface. The flesh is very firm, crisp and juicy. The taste is very good. The flavor is aromatic with high sugar content and balanced acidity level. 'Majesty' has a very good ability for long term storage.

4 Drawing Sheets

Latin name of the genus and species of the plant claimed: *Malus domestica* Mill.

Variety denomination: 'Majesty'.

PRIORITY CLAIM

This application claims priority to European Community Plant Variety Office Application No. 2012/0807 filed Apr. 10, 2012, the disclosure of which is incorporated by reference herein in its entirety.

BACKGROUND OF THE INVENTION

The present invention relates to a new and distinct variety of apple tree, botanically known as *Malus domestica* Mill. of the Family Rosaceae, and hereinafter referred to by the variety denomination 'Majesty'.

The new *Malus* variety is a product of a planned breeding program conducted by the inventors, Michelangelo Leis, Alessio Martinelli, Francesco Tagliani, and Gianfranco Castagnoli in S. Giuseppe di Comacchio (Ferrara), Italy. The objective of the breeding program was to develop new *Malus* varieties with improved production characteristics, high-quality flavour and aroma and sustainability by increasing the tree's natural resistance. The primary objective of the Applicant's research program is to selection new apple varieties with natural resistances, in particular to scab.

The new *Malus* variety 'Majesty', originated from a cross made in a planned, controlled breeding program in S. Giuseppe di Comacchio (Ferrara), Italy. The female parent is the apple tree variety 'Co-op 25' (patented; U.S. Plant Pat. No. 12,323). The male parent is an unpatented, proprietary selection denominated 'CIVCP-142'. 'Majesty' was discovered and selected in October 2000 by the inventors as a flowering plant within the progeny of the stated cross in a controlled environment in S. Giuseppe di Comacchio (Ferrara), Italy.

Asexual reproduction of the new *Malus* variety by budding and grafting was first performed in August 2001 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'Majesty' which in combination distinguish this apple tree as a new and distinct variety:

1. Bi-colored variety with intense red-purple overcolor;
2. Big size;
3. Weak vigor, open habit with short branches, easy to manage;
4. High sugar content and
5. Long storage ability.

When compared to plants of the parent varieties, the claimed variety 'Majesty' differs primarily in the traits listed in Table 1 below:

TABLE 1

| Comparison to parent varieties | | | |
|---|---|---|---|
| Characteristic in which the variety is different | State of expression of candidate variety | The female parent ('Co-op 25') | The male parent ('CIVCP-142') |
| Resistance to scab | Not | Yes | Not |
| Fruit: over color | Purple red | Red | Light red |
| Fruit: relative area of over color | Large | Medium | Small to medium |
| Time of eating maturity | Late | Medium | Late to very late |

When compared to plants of the related variety 'SINFONIA' (U.S. Plant patent application Ser. No. 13/986,176), the claimed variety differs primarily in the traits listed in Table 2 below:

TABLE 2

| Comparison to related cultivar 'SINFONIA' | | | |
|---|---|---|---|
| Denomination of sibling cultivar | Characteristic in which the sibling cultivar different | State of expression of sibling cultivar | State of expression of candidate variety |
| 'Sinfonia' | Time of eating maturity | Medium to late (twenty days before 'Majesty') | Late |
| | Fruit: overcolor | Orange red | Red - Purple |
| | Fruit: size | Very large | Large |

Of the commercial cultivars known to the inventors, the most similar in comparison to the new apple tree variety 'Majesty' is the variety 'Cripps Pink' (patented; U.S. Plant Pat. No. 7,880). In comparison to the similar variety 'Cripps Pink', 'Majesty' differs primarily in the traits listed in Table 3 below:

TABLE 3

| Comparison to Similar Variety | | | |
|---|---|---|---|
| Denomination of similar variety | Characteristic in which the similar variety is different | State of expression of similar variety | State of expression of candidate variety |
| 'Cripps Pink' | Time of eating maturity | Very late | Late (one month before) |
| | Fruit: overcolor | Pink red | Red - Purple |
| | Tree: vigor | Medium | Weak |

BRIEF DESCRIPTION OF THE DRAWINGS

The accompanying photographs illustrate the overall appearance of the new apple tree 'Majesty' showing the colors as true as is reasonably possible with color reproductions of this type. Color in the photographs may differ slightly from the color value cited in the detailed botanical description, which accurately describe the color of 'Majesty'. In the photographs a label shows the breeder's reference for 'Majesty', 'YX-4'.

DETAILED BOTANICAL DESCRIPTION

Figure 1:
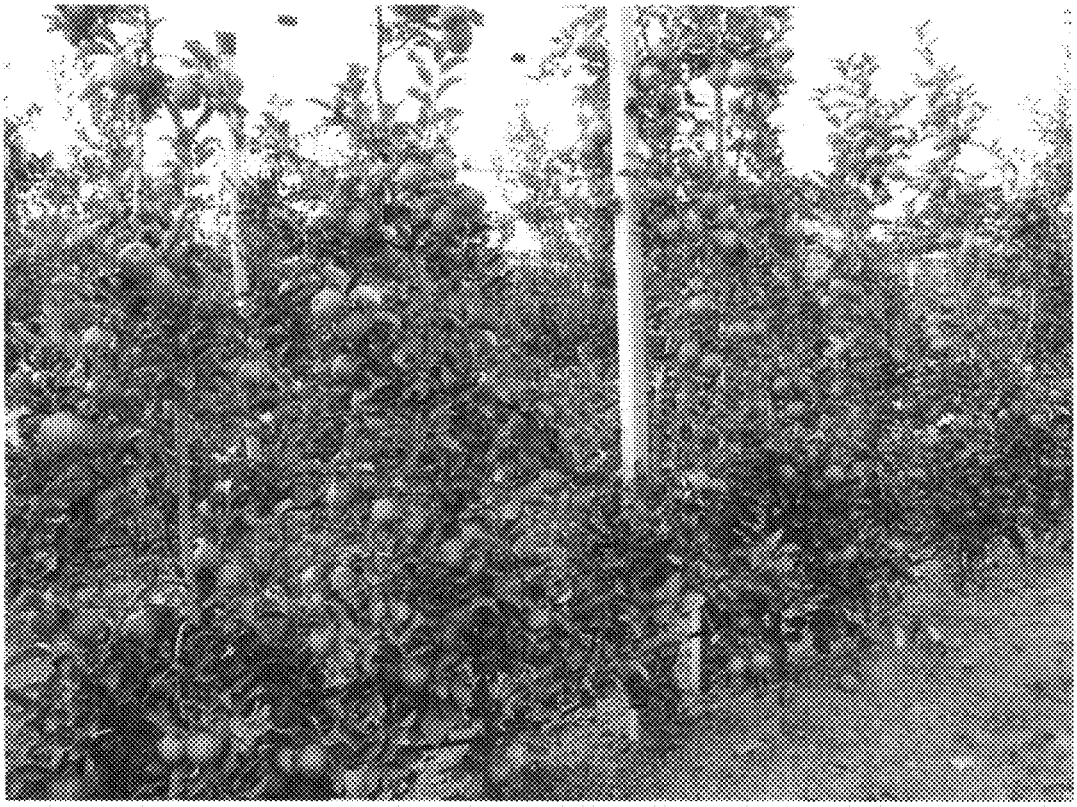
FIG. 1: illustrates the plant of 'Majesty'.
Figure 2:
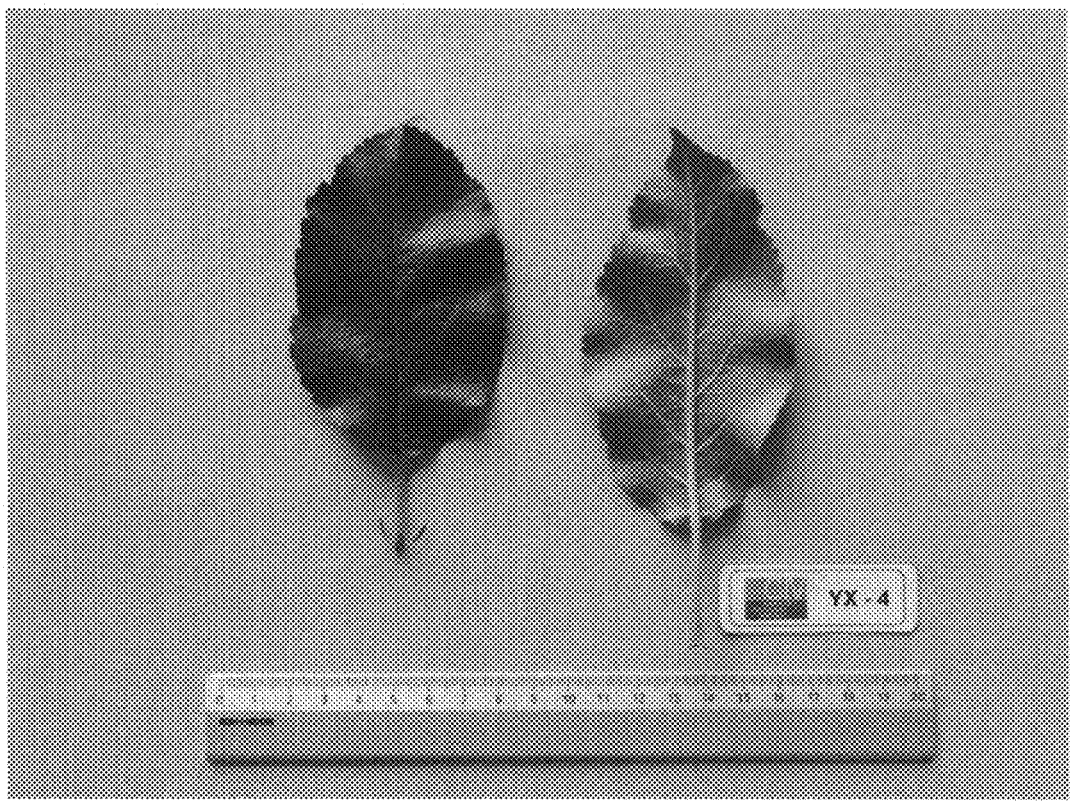
FIG. 2: illustrates the leaves of 'Majesty'.
Figure 3:
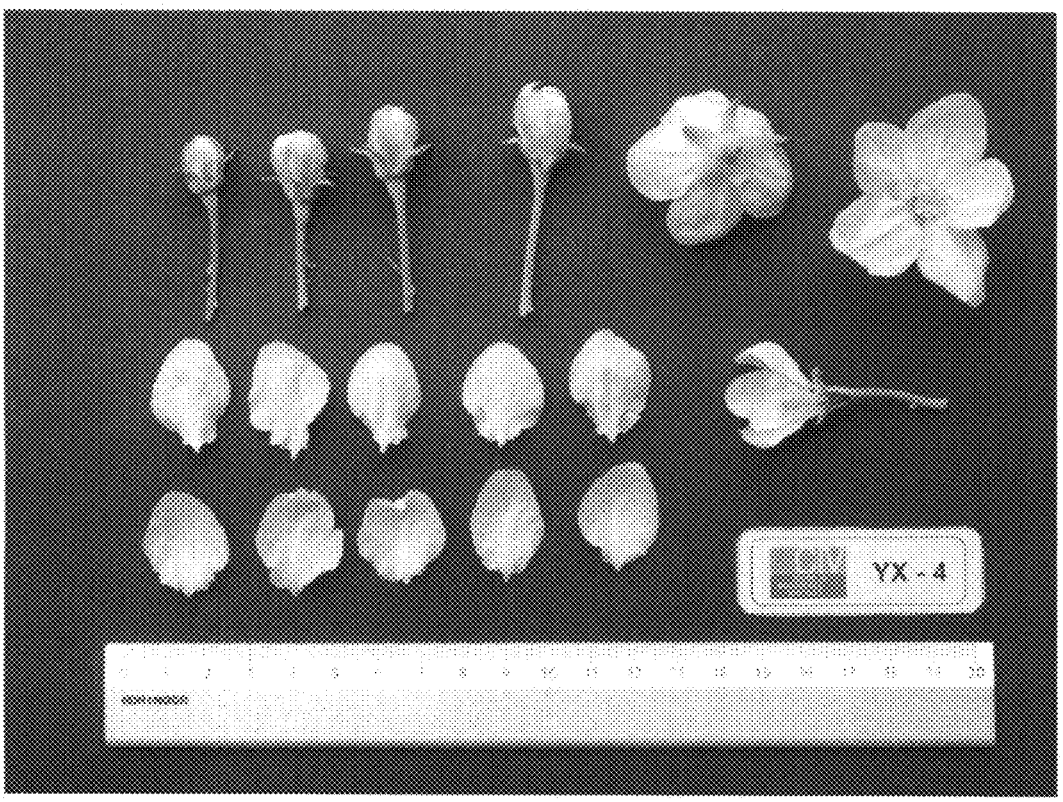
FIG. 3: illustrates the flowers of 'Majesty
Figure 4:
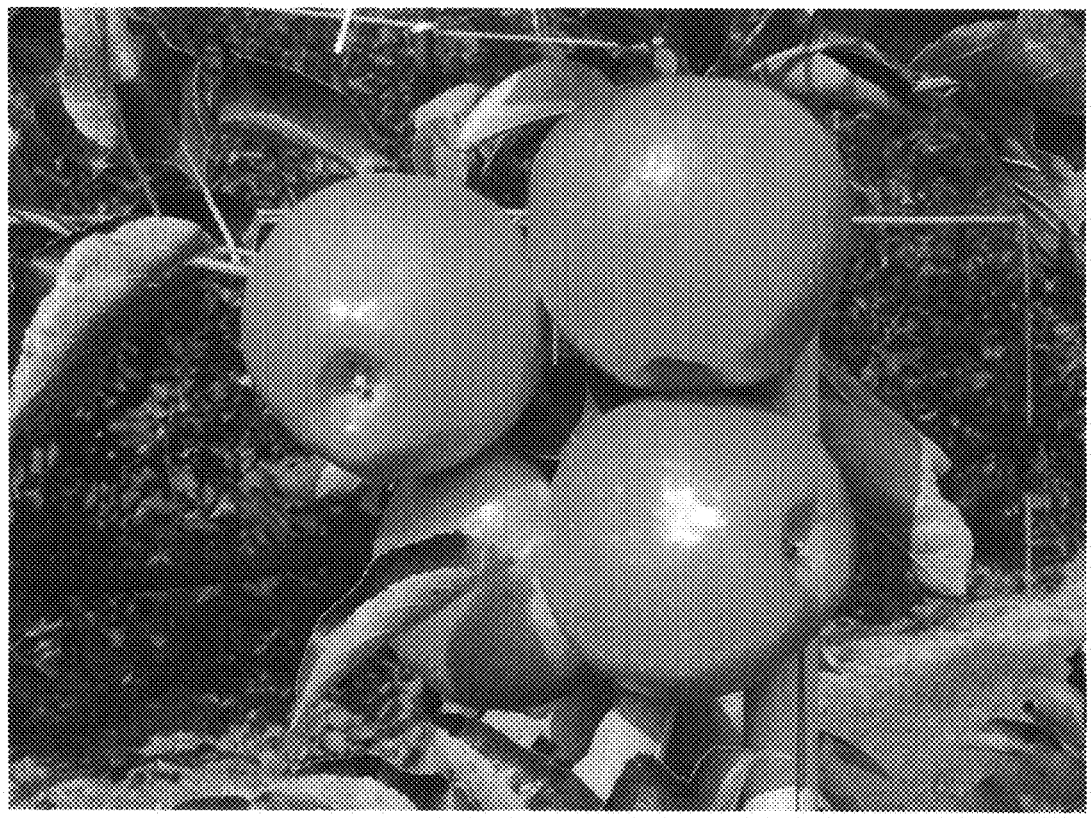
' and
FIG. 4: illustrates the fruits of 'Majesty'.

The new *Malus* variety 'Majesty' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'Majesty' as grown in the apple farm in S. Giuseppe di Comacchio (Ferrara), Italy, under conditions which closely approximate those generally used in commercial practice. The apple farm where 'Majesty' is grown is situated near the Adriatic sea (44°45' North, 12°11' East) and is zero (0) meters above sea level. The soil of the apple farm where 'Majesty' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'Majesty' trees that were grown in the apple farm in S. Giuseppe di Comacchio (Ferrara), Italy, from 2007 to 2011 All trees were of cropping maturity. Quantified measurements are expressed as an average of measurements taken from a number of individual trees of 'Majesty'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in S. Giuseppe di Comacchio (Ferrara), Italy.

All trees of 'Majesty', insofar as they have been observed, have been identical in all the characteristics described below.

Classification:

*Botanical.*—*Malus domestica* Mill.

Parentage:

*Female parent.*—*Malus domestica* Mill. 'Co-op 25' (patented; U.S. Plant Pat. No. 12,323).

*Male parent.*—*Malus domestica* Mill. 'CIVCP-142' (unpatented, proprietary selection).

Propagation: Budding and grafting on M9 rootstock.

Tree:

*Age.*—Observed plants were four years old.

*Vigor.*—Weak to medium.

*Tree type.*—Ramified.

*Habit.*—Spreading, branches angle is typically 45° to 55° degrees from the vertical stem.

*Density.*—Medium density.

*Cropping behavior.*—Precocious fruit bearing with high productivity.

*Type of bearing.*—Long shoot and spur on 2-3 year old shoots.

*Production.*—$4^{th}$ year: about 15-16 Kg.

*Size.*—Height: 3.0 m. Spread: 1.20 m. Trunk Diameter: about 39 mm as measured 20 cm above point of grafting.

*Surface texture.*—Smooth.

*Bark color.*—Grey brown group RHS 199 C.

*Trunk lenticels.*—

*Overall shape.*—Round to elongated. Length: 1.7 mm. Width: 1.2 mm. Color: greyed-orange RHS 165 B. Density: 2 to 3 per $cm^2$.

*Branches.*—Number per tree: about 20 at four (4) years. Length: Varies due to pyramidal shape of tree. At four (4) years, maximum of 80 cm to 100 cm; minimum of 40 cm to 60 cm. Diameter (at 3 years): About 10 mm to 12 mm. Surface texture: smooth. Color (at 3 years): brown RHS 200 D. Internode length: About 1.8 cm to 2.5 cm. Internode diameter: About 8.0 mm to 10 mm.

*Branches lenticels.*—Length: 1.0 mm. Width: 0.5 mm. Color: grey-brown RHS 199 A. Density: About 3-4 per $cm^2$.

Leaves:

*Arrangement.*—Alternate, simple, petiolated.

*Lamina.*—Size: Length (4 year old): 92.5 mm (from $3^{rd}$ to $5^{th}$ fully expanded leaf). Width (4 year old): 61.8 mm (from $3^{rd}$ to $5^{th}$ fully expanded leaf). Length/width ratio: 1.50. Overall Shape: broad-elliptical. Base shape: broad. Apex shape: acuminate. Margin: serrate. Pubescence: absent on upper surface and weak pubescent on lower surface. Attitude in relation to shoot: outwards. Color (mature leaves): green RHS 139 A on the upper side and 148 B underside. Color (immature leaves): green RHS 141 A on the upper side and 138 A underside.

*Venation.*—Type: prominent pinnate venation from a midrib to the edge. Color: yellow-green, RHS 148 D.

*Petiole.*—Length: average 30.9 mm. Diameter: average 1.9 mm. Texture: hairy. Color: yellow-green RHS 148 C with anthocyanin coloration RHS 46 A red group.

*Stipule.*—Arrangement: adnate, grown together; medium size. Distance of stipules from basal attachment of petiole: attached to the base. Length: 5 to 10 mm. Width: 0.5 to 1.0 mm.

Spur:

*Present.*—On 2-3 year old shoots.

*Distance between each spur.*—On the two-three year old branches, the distance is about 20 mm to 50 mm.

*Number of fruit per spur.*—4 to 5 without thinning.

Flowers:

*Blooming time.*—Full bloom on April $2^{nd}$ in S. Giuseppe di Comacchio (Ferrara), Italy, in year 2012.

*Blooming period.*—8 to 10 days.

*Fragrance.*—Slight.

*Type.*—Corymb.

*Number of flowers per corymb.*—5 to 6.

*Flower size.*—Diameter: about 45 mm. Flower depth (height of the corolla): about 9 mm, measured when the flowers are fully open. Flower color: Primarily white RHS 155D, when petals are fully opened, undersides of petals there are shades red-purple RHS 54 A. In balloon stage the color is red-purple RHS 60 C.

*Buds.*—Number of buds per spur: typically, one per spur. Shape: pointed. Length: about 8 mm. Width: about 4 mm. Color: brown, RHS 200 B with hairy surface.

*Petals.*—Arrangement: overlapping. Number per flower: five (5). Length: average 26.3 mm. Width: average 19.1 mm. Length/width ratio: 1.38. Overall shape: ovate. Apex shape: obtuse. Base shape: rounded. Texture: smooth. Margin: entire. Color (upper surface): white RHS 155 D. Color (lower surface): white RHS 155 D with shade red-purple RHS 54 A.

*Sepals.*—Number per flower: five (5). Length: average 10.4 mm. Width: average 4.4 mm. Length/width ratio: 2.36. Overall shape: lanceolate. Apex shape: acute. Texture: hairy. Margin: entire. Color: yellow-green RHS 146 B, same color for upper and lower surface.

*Pedicel.*—Length: 25 mm to 29 mm. Diameter: about 2 mm. Texture: hairy. Color: green RHS 138 C.

Fruit:

*Keeping quality.*—The fruits can be stored in cold temperature conditions without loosing firmness and juiciness. It has a long shelf life, up to two weeks.

*Maturity when described.*—Ripe for eating.

*Maturity period after full bloom.*—About 187 days in S. Giuseppe di Comacchio (Ferrara), Italy in 2012.

*Date of first and last pickings.*—5 October the first picking and 10 October last picking in S. Giuseppe di Comacchio (Ferrara), Italy (North 44°45'46.2", East 012°11'31.9") in year 2012.

*General shape.*—Globose.

*Average weight.*—244 g.

*Fruit size.*—Average height: 87 mm. Average diameter (at widest point): 79.6 mm.

*Position of maximum diameter.*—In the middle.

*Height/diameter ratio.*—1.09.

*Stem.*—Length: average 29.5 mm. Diameter: about 2.5 mm. Color: yellow-green RHS 145 A.

*Stalk cavity.*—Depth: average 16.9 mm. Width: average 38.0 mm.

*Eye basin.*—

*Aperture of eye.*—Closed. Depth: average 10.43 mm. Width: average 31.6 mm. Crowning at calyx end: medium. Position of sepals: erect and converging. Calyx tube: funnel form.

*Skin.*—Thickness: medium. Texture: smooth or slight rough. Bloom: absent or very weak. Greasiness: absent or very weak. Firmness (at picking time): 8 to 9 kg/$cm^2$. Overcolor color: purple red RHS 53 B. Percentage of skin surface with overcolor color: large. Pattern of overcolor: solid flush with weakly defined stripes. Intensity of overcolor: medium. Ground color: yellow-green, RHS 145 C.

*Skin lenticels.*—Length: about 0.5 mm. Width: about 0.5 mm. Color: greyed-orange RHS 163 C. Density: about 2-3 per $cm^2$ in the central area of the surface of fruit. The number of lenticels increases in a direction toward the hollow of the calyx and the size of the lenticels decreases.

*Flesh.*—Color: yellow RHS 11 D. Texture: fine. Tipe of flesh: crisp and juicy. Firmness: firm. Aroma: intense. Eating quality: the flavour is aromatic with high sugar content and balanced acidity level. Sugar content (at picking time): about 14° Brix. Acidity/Starch (at picking time): Acidity: 4.5 to 5.5 g/l Malic acid/starch: 4 (Laimburg scale 1 to 5).

*Core.*—Symmetry of core: slightly asymmetric. Distinctness of core lines: not very evident. Locules: Number (per fruit): 5 (five). Length: average 9.5 mm. Width: average 3.5 mm. Form: moderately open.

Seeds:

*Number per fruit.*—7 to 9.

*Number per locule.*—1 or 2.

*Shape.*—Elliptic.

*Length.*—Average 10.5 mm.

*Width.*—Average 5.0 mm.

*Color.*—Greyed-orange RHS 165 B.

Reproductive organs:

*Androecium.*—Stamens: Number per flower: about 18-20. Length: average 11.0 mm. Filament: Length:

average 10.0 mm. Anther: Shape: ovoid, flat in the center. Length: average 2.0 mm. Diameter: 1.5 mm. Color: yellow RHS 10 C. Pollen: Amount: abundant. Color: yellow RHS 10 C. Requirements: the crab apple *Malus* 'Evereste' is good pollinator.

*Gynoecium.*—Stigma: Shape: funnel shape with receptive surface on top. Length: 0.9 mm. Width: 0.5 mm. Color: yellow-green, RHS 144 D. Style: Number per flower: 5 (Five). Length: about 9.5 mm. Width: about 0.3 mm. Color: yellow-green, RHS 144 D. Ovary: Length: about 3.5 mm. Width: about 2.5 mm. Color: yellow-green, RHS 144 A.

Use: Fresh market.

Sensitivity to disease/pests: No particular sensibilities detected.

Winter hardiness: Tolerance to temperatures of −12° C. without observed damage to wood and buds of dormant apple trees; but open flowers and young fruitlets are killed by exposure to −3° C. to −5° C., depending on the length of exposure.

Drought/heat tolerance: Good tolerance to heat, up to 40° C., growth is limited by drought periods without irrigation.

Shipping/storage characteristics: Very good storability under ULO-conditions (1° C., 2% $0_2$, 2% $CO_2$) for up to seven (7) months.

We claim:

1. A new and distinct *Malus domestica* Mill. apple tree named 'Majesty', substantially as illustrated and described herein.

* * * * *